United States Patent [19]

Imai et al.

[11] 4,374,287
[45] Feb. 15, 1983

[54] SYNTHESIS OF ALCOHOLS

[75] Inventors: Tamotsu Imai, Mt. Prospect; Edwin H. Homeier, Maywood, both of Ill.

[73] Assignee: UOP Inc., Des Plaines, Ill.

[21] Appl. No.: 237,561

[22] Filed: Feb. 24, 1981

Related U.S. Application Data

[63] Continuation of Ser. No. 163,762, Jun. 27, 1980, abandoned.

[51] Int. Cl.$^3$ .............................................. C07C 27/22
[52] U.S. Cl. .................................................. 568/909
[58] Field of Search ........................................ 568/909

[56] References Cited

U.S. PATENT DOCUMENTS 4,275,252  6/1981  Imai et al. ............................. 568/909
4,292,196  9/1981  Homeier et al. ..................... 568/909

*Primary Examiner*—Joseph E. Evans
*Attorney, Agent, or Firm*—James R. Hoatson, Jr.; Raymond H. Nelson; William H. Page, II

[57]  ABSTRACT

Alcohol may be synthesized by treating olefinic hydrocarbons with carbon monoxide and hydrogen in a hydroformylation zone utilizing a rhodium complex catalyst to effect the reaction. Following formation of the alcohol, the catalyst may be extracted from the alcohol by treatment with an aqueous ammonium hydroxide solution. Thereafter the aqueous ammonium hydroxide solution containing the catalyst is then stripped of ammonia by treatment with carbon monoxide or carbon monoxide containing gas. The aqueous ammonium hydroxide solution containing the rhodium complex catalyst is then stripped of a portion of water and the remaining solution is thereafter recycled to the hydroformylation zone.

13 Claims, 1 Drawing Figure

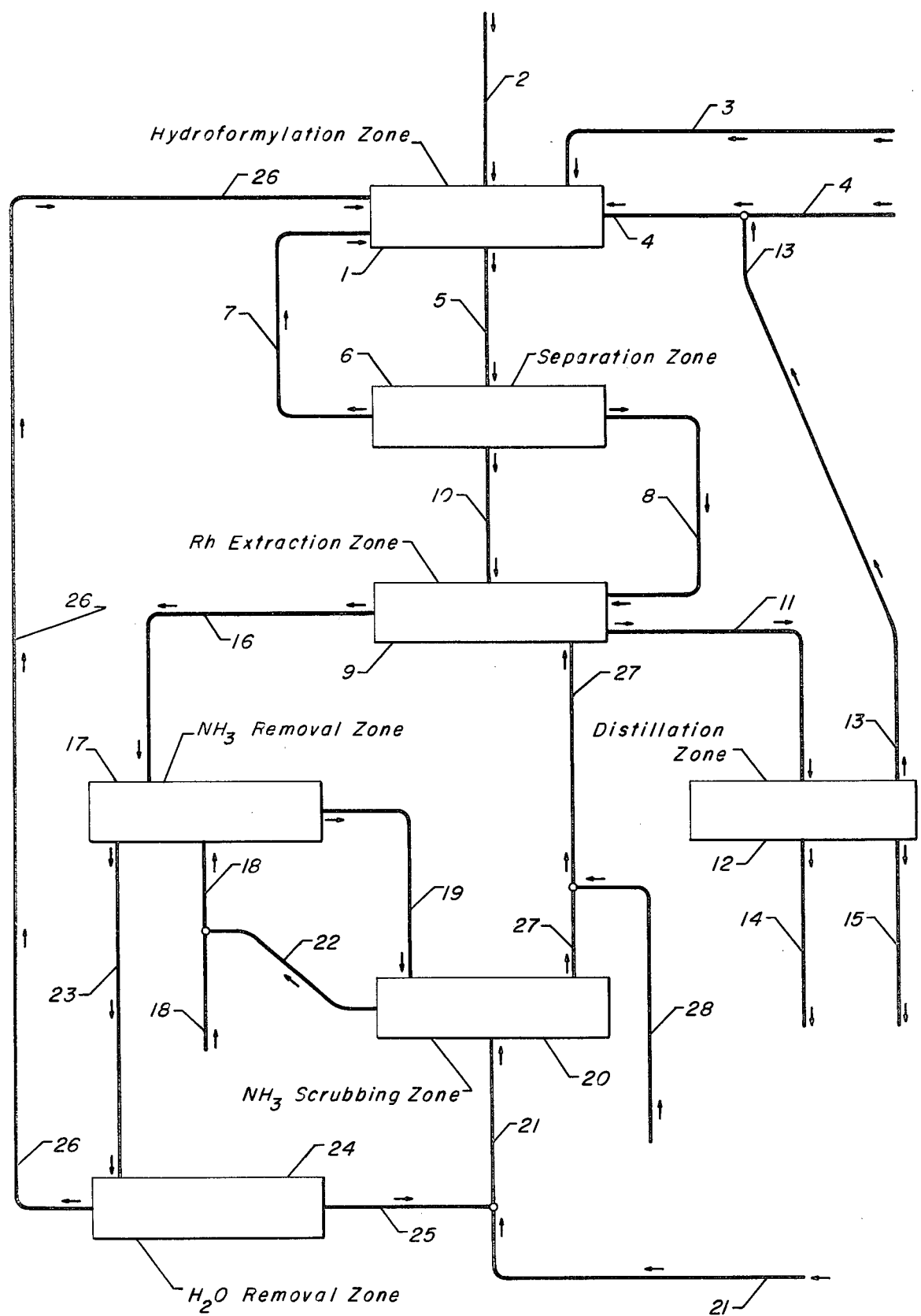

SYNTHESIS OF ALCOHOLS

RELATED APPLICATIONS

This application is a continuation of our copending application, Ser. No. 163,762 filed June 27, 1980 and now abandoned.

DESCRIPTION OF THE INVENTION

This invention relates to a process for the synthesis of alcohols. More specifically, the invention is concerned with a process for synthesizing alcohols by treating an olefinic hydrocarbon with carbon monoxide and hydrogen in the presence of a rhodium complex catalyst, said catalyst then being recovered in a series of steps hereinafter set forth in greater detail and recycled for further use.

Alcohols are important basic chemicals which find a wide variety of uses in industry. For example, ethyl alcohol is a basic chemical which is used as a solvent and in the manufacture of intermediates, dyes, synthetic drugs, synthetic rubbers, detergents, cleaning source, surface coatings, cosmetics, pharmaceuticals, rocket fuel, beverages, etc. Isopropyl alcohol is used in the manufacture of acetone which in turn is a source of acetic anhydride, diacetone alcohol, methyl isobutyl ketone and other derivatives. It is also used as a solvent for essential oils, gums, resins; as a latent solvent for cellulose derivatives; as an anti-stalling agent in liquid fuels or as an intermediate in the manufacture of pharmaceuticals, perfumes, lacquers, rocket fuel, etc. Likewise, dodecyl alcohol which is also known as lauryl alcohol is used in the manufacture of synthetic detergents, lube additives, pharmaceuticals, rubber, textiles, and perfumes. Tetradecanol which is also known as myristyl alcohol is used in organic synthesis, as a plasticizer, antifoam agent, as a perfume fixitive for soaps and cosmetics as well as other uses.

The prior art has shown, as exemplified by the Oxo process, that aldehydes may be produced from olefinic hydrocarbons by treatment with carbon monoxide and hydrogen using a cobalt carbonyl catalyst. It has further been shown in the prior art, as exemplified by U.S. Pat. No. 2,880,241, that rhodium is known to be a much more active catalyst than cobalt. The activity and selectivity of rhodium catalysts may be altered by modifying the catalyst with other compounds such as tertiary amines. For example, when using tertiary amines to modify rhodium catalysts, it is possible to produce alcohols rather than aldehydes in this process.

The commercialization of processes for the synthesis of alcohols utilizing rhodium complex catalysts is affected by the difficulty which is attendant in the recovery of rhodium, a particular disadvantage which negates the commercial use of such catalyst complexes comprising the frequent losses of the precious metal which may occur under process conditions, the loss of only a trace amount of this precious metal making the process uneconomical to operate and overshadowing the technological attractive conversion rate and selectivity rate which is obtained when using this metal. The separation of the rhodium catalyst from alcohol products, especially high molecular weight alcohols by conventional means such as distillation, is not practical inasmuch as the unstable rhodium-amine complex decomposes in a distillation apparatus, thus resulting in the loss of the rhodium by plating or precipitation on the surfaces of the processing equipment.

Inasmuch as a particular advantage of utilizing a one-step synthesis of alcohol lies not only in a lower process cost and capital cost, when compared with the conventional Oxo process to produce aldehydes, but also results in a higher yield of the desired products. This is particularly advantageous inasmuch as a loss of aldehydes which easily takes place during distillation via their condensation in a still does not occur in this process.

It is therefore an object of this invention to provide a process for the synthesis of alcohol utilizing a recovery system for the catalyst.

A further object of this invention is found in a one step process for the synthesis of alcohols utilizing a precious metal catalyst such as a rhodium complex catalyst which is easily recoverable and reusable in the process.

In one aspect an embodiment of this invention resides in a process for the synthesis of an alcohol which comprises the steps of treating an olefinic hydrocarbon with carbon monoxide and hydrogen in a hydroformylation zone at hydroformylation reaction conditions in the presence of a rhodium complex catalyst; extracting said rhodium complex catalyst from the resulting alcohol by treatment with an aqueous ammonium hydroxide solution at treating conditions; recovering said alcohol; stripping ammonia from said aqueous ammonium hydroxide solution containing said rhodium complex catalyst by treatment with a stripping agent at stripping conditions; stripping a portion of water from said aqueous solution containing said rhodium complex catalyst; recycling the rhodium complex catalyst to said hydroformylation zone.

A specific embodiment of this invention is found in a process for the synthesis of an alcohol which comprises treating hendecene with carbon monoxide and hydrogen in a hydroformylation zone at a temperature in the range of from about 50° to about 250° C. and a pressure in the range of from about 50 to about 300 atmospheres in the presence of a catalyst comprising chlorodicarbonylrhodium dimer, extracting said catalyst from the resulting dodecanol by treatment with an aqueous ammonium hydroxide solution at a temperature in the range of from about 20° to about 100° C. and a pressure in the range of from about atmospheric to about 50 atmospheres, stripping ammonia from said aqueous ammonium hydroxide solution which contains said catalyst by treatment with carbon monoxide at a temperature in the range of from about 20° to about 150° C. and a pressure in the range of from about 0.1 to about 5 atmospheres, stripping a portion of water from the aqueous solution containing said catalyst at a temperature in the range of from about 50° to about 150° C. and a pressure in the range of from about 1 to about 5 atmospheres, and recycling the rhodium complex catalyst to said hydroformylation zone.

Other objects and embodiments will be found in the following further detailed description of the present invention.

As hereinbefore set forth the present invention is concerned with a process for the synthesis of alcohols utilizing a rhodium complex catalyst which may be recovered and recycled for further use. The synthesis of the alcohols is effected by reacting an olefinic hydrocarbon with carbon monoxide and hydrogen in the presence of these rhodium complex catalysts and a promoter or modifier comprising a tertiary amine. The reaction conditions which are employed to synthesize the alcohol will include a temperature of from about 50° to about 250° C. and a pressure in the range of from about 50 to about 300 atmospheres. In the preferred embodiment of the invention the pressures which are employed to effect the desired result will be the autogenous pressures resulting from the presence of hydrogen and carbon monoxide in the reaction mixture. However, it is also contemplated within the scope of this invention that the pressures resulting from the use of hydrogen and carbon monoxide will comprise only a partial operating pressure, the remainder being provided for by the introduction of substantially inert gas such as nitrogen, helium, argon, etc., into the reaction vessel. In addition, other reaction conditions which are present during the synthesis of the alcohol will include a mole ratio of hydrogen to carbon monoxide in the range of from about 0.5:1 to about 5:1 moles of hydrogen per mole of carbon monoxide, a mole ratio of olefin to catalyst in the range of from about 500:1 to about 3000:1 moles of olefin per mole of catalyst and a mole ratio of tertiary amine modifier to catalyst in the range of from about 50:1 to about 300:1 moles of amine per mole of catalyst.

Examples of olefinic hydrocarbons which may be employed to effect the process of this invention will include straight chain and branched chain olefins containing from 2 to about 30 carbon atoms such as ethylene, propylene, butene-1, butene-2, isobutylene, pentene-1, pentene-2, isopentene isomers, hexene-1, hexene-2, hexene-3, heptene-1, heptene-2, heptene-3, octene-1, octene-2, octene-3octene-4, nonene-1, nonene-2, nonene-3, nonene-4, as well as the isomeric decenes, undecenes, dodecenes, tridecenes, tetradecenes, pentadecenes, hexadecenes, heptadecenes, octadecenes, nonadecenes, eicosenes, henicosenes, docosenes, tricosenes, tetracosenes, pentacosenes, hexacosenes, heptacosenes, octacosenes, nonacosenes, triacontenes, etc.

The reaction between the olefinic hydrocarbon of the type hereinbefore set forth, carbon monoxide and hdrogen is effected in the presence of a rhodium complex catalyst which may be organometallic in nature or which may comprise a salt, oxide, or rhodium metal which is converted to the complex catalyst during the process under the reaction conditions employed. Specific examples of these rhodium catalysts will include rhodium nitrate, rhodium chloride, rhodium bromide, rhodium iodide, rhodium fluoride, chlorodicarbonylrhodium dimer, rhodium carbonyl, chlorobis(ethylene)rhodium dimer, hexarhodium hexadecylcarbonyl, tetrarhodiumdodecylcarbonyl, rhodium acetate, rhodium acetylacetonate, rhodium black, etc. The modifier which is utilized to selectively form alcohols will comprise a tertiary amine, said tertiary amine including alkyl amines, aryl amines, heterocyclic amines, cycloalkyl amines, etc., such as trimethylamine, triethylamine, tripropylamine, the isomeric tributylamines, tripentylamines, trihexylamines, triheptylamines, trioctylamines, trinonylamines, tridecylamines, dimethylethylamine, dimethylpropylamine, dimethylbutylamine, dimethyldodecylamine, triphenylamine, tribenzylamine, tri-o-tolylamine, tri-m-tolylamine, tri-p-tolylamine, tricyclopentylamine, tricyclohexylamine, N-methylpiperidine, N-methylpyran, N-ethylpiperidine, N-ethylpyran, etc. It is to be understood that the aforementioned olefinic hydrocarbons, rhodium catalysts and teriary amines are only representative of the class of compounds which may be employed and that the present invention is not necessarily limited thereto.

After synthesizing the alcohol utilizing the desired reactants, catalysts and operating conditions, the product is recovered and the rhodium complex catalyst is separated therefrom and recovered by extracting the rhodium complex catalyst from the alcohol by treating the alcohol with an aqueous ammonium hydroxide solution. This step of the process is effected at treating conditions which will include a temperature in the range of from about ambient (20°-25° C.) to about 100° C. and a pressure in the range of from about atmospheric to about 50 atmospheres. In the event that superatmospheric pressures are employed in the treating step, the pressures are afforded by the introduction of a substantially inert gas such as nitrogen into the reaction vessel. After allowing the treatment to take place during a period which may range from about 0.5 up to about 20 hours or more, the aqueous ammonium hydroxide solution which contains from about 5 to about 50% by weight of ammonia is stripped of said ammonia by treatment with a stripping agent. The stripping of the ammonia from the aqueous ammonium hydroxide solution is accomplished inasmuch as if the ammonia is allowed to remain in the solution the interaction or chemical affinity between the ammonia and the rhodium present in the rhodium complex catalyst is so strong as to prevent the extraction of the rhodium catalyst in the hydroformylation zone. The ammonia must be stripped from the solution so that less than about 0.5% by weight ammonia remains therein. By removing ammonia from the solution the rhodium complex will migrate from the aqueous ammonium hydroxide solution to the organic phase in a subsequent step hereinafter set forth in more detail. The stripping of the ammonia is accomplished by treatment with a stripping agent which may comprise carbon monoxide or a carbon monoxide-containing gas such as a mixture of carbon monoxide and hydrogen, carbon monoxide and nitrogen, carbon monoxide and helium, carbon monoxide and argon, etc. The stripping is effected at temperatures which may range from about ambient up to about 150° C. and at pressures ranging from about 0.1 to about 5 atmospheres.

Following the stripping of the ammonia, the aqueous solution containing the rhodium complex catalyst and less than about 0.5% by weight of ammonia is then subjected to a water stripping step. The stripping of the water from the aqueous solution containing the rhodium complex catalyst is effected at stripping conditions which, in the process of this invention, will comprise a distillation step at a temperature of from about 50° to 150° C. and a pressure in the range of from about 0.5 to about 5 atmospheres. After stripping a portion of the water, the remaining solution is then recycled to the hydroformylation zone for use as a catalyst in the aforementioned hydroformylation reaction whereby the hydrocarbons are converted into alcohols.

The process of this invention may be effected in any suitable manner and may comprise either a batch or a continuous type operation. For example, when a batch type operation is used, a quantity of the olefin which is to be hydroformylated is charged to a pressure resistant apparatus such as an autoclave of the rotating, mixing or stirring type, said apparatus containing the rhodium complex catalyst and the tertiary amine which acts as a modifier. The autoclave is sealed and carbon monoxide and hydrogen pressured in until the desired operating pressure has been attained. Thereafter the reactor is heated to the desired operating temperature and maintained thereat for a predetermined period of time which may range from about 0.5 up to about 10 hours or more in duration. Following the completion of the desired reaction period, heating is discontinued and after the apparatus has returned to room temperature the excess pressure is discharged and the reaction mixture is recovered therefrom. The reaction mixture is then charged to a second apparatus which may also be of the pressure resistant type, if so desired, and the reaction mixture is contacted with an aqueous ammonium hydroxide solution at reaction conditions hereinbefore set forth in greater detail. Upon completion of the extraction or treatment period the aqueous ammonium hydroxide solution containing the extracted rhodium complex catalyst is separated from the organic phase which comprises the product alcohol and the amine modifier. The latter may then be subjected to fractional distillation to remove the amine modifier and passed to storage while the former is then placed in a third apparatus wherein the aqueous ammonium hydroxide solution containing the rhodium complex catalyst is stripped by treatment with carbon monoxide. The stripping operation is also effected at reaction conditions hereinbefore set forth for a period of time which may range from about 0.5 to about 10 hours or more in duration, the ammonia being removed during this time until an amount less than about 0.5% by weight remains. The substantially ammonia free aqueous ammonium hydroxide solution is then placed in a water stripping apparatus which may comprise a distillation column in which a portion of the water is removed, the remaining solution comprising essentially a rhodium complex catalyst may then be utilized in further hydroformylation reactions.

It is also contemplated within the scope of this invention that the process of the present invention may be effected in a continuous manner of operation. When such a type of operation is employed the starting material comprising olefinic hydrocarbon is continuously charged to a reaction zone which is maintained at the proper operating conditions of temperature and pressure and which contains a rhodium complex catalyst as well as a tertiary amine modifier. The desired operating pressures are attained by utilizing the autogenous pressures afforded by the carbon monoxide and hydrogen which are required for the hydroformylation reaction. After passage through the reaction zone for a predetermined period of time the reactor effluent is continuously withdrawn and passed to an extraction zone wherein said effluent is contacted or treated with an aqueous ammonium hydroxide solution also continuously charged to said zone. After passage through the extraction zone the aqueous layer comprising the ammonium hydroxide solution containing the rhodium complex catalyst is separated from the organic phase which comprises the product alcohol and the tertiary amine modifier. The latter is then continuously charged to a distillation zone wherein the tertiary amine modifier is separated from the product alcohol and recycled to the reaction zone while the product alcohol is withdrawn and a major portion thereof is recovered for storage. The aqueous phase is continuously charged to a stripping zone wherein it is contacted with carbon monoxide or a carbon monoxide-containing gas at stripping conditions whereby any free ammonia present in the ammonium hydroxide solution is stripped therefrom. The stripped aqueous ammonium hydroxide solution containing the rhodium complex catalyst is continuously withdrawn from the stripping zone and passed to a second $H_2O$ removal zone wherein a portion of the water in the solution is removed, the remainder of the solution being recycled back to the hydroformylation reaction zone for use as a catalyst therein. It is to be noted that the extraction of the rhodium complex catalyst from the aqueous ammonium hydroxide phase to the organic phase in the hydroformylation zone is also effected under a carbon monoxide pressure which may range from about atmospheric to about 300 atmospheres, thereby assuring a more complete extraction of the catalyst from the aqueous phase to the organic phase. The aqueous ammonium hydroxide solution may then be recycled back to the first extraction zone for use as the extractant in recovering the rhodium complex catalyst from the alcohol phase.

BRIEF DESCRIPTION OF THE DRAWING

The present invention will be further illustrated with reference to the accompanying drawing which sets forth a flow diagram of one embodiment of the process of this invention. It is to be understood that various valves, pumps, etc., have been eliminated as not being essential to the complete understanding of the invention. However, the utilization of these as well as other similar appurtenances will become obvious as the drawing is described.

Referring now to the drawing, an olefinic hydrocarbon which is to be hydroformylated according to the process of this invention is charged to hydroformylation zone 1 through line 2 along with any make-up rhodium complex catalyst of the type hereinbefore set forth. In addition, carbon monoxide and hydrogen are also charged to reaction zone 1 through line 3. In zone 1, the olefinic hydrocarbon is subjected to a hydroformylation reaction at conditions hereinbefore set forth in the presence of a rhodium complex catalyst which has been modified by the addition of a tertiary amine, said tertiary amine being charged to reaction zone 1 through line 4. After passage through the reaction zone for a predetermined period of time, the reaction mixture is withdrawn from zone 1 through line 5 and passed to separation zone 6. In separation zone 6 any unreacted carbon monoxide and hydrogen are separated and recycled to zone 1 through line 7. In addition, some water containing a trace of the rhodium complex catalyst is withdrawn from zone 6 through line 8 and passed to rhodium extraction zone 9. The organic product is withdrawn from zone 6 through line 10 and also passed to zone 9. In zone 9 the organic phase is contacted with an aqueous ammonium hydroxide solution which is charged to zone 9 through line 27 from a source hereinafter set forth in greater detail. After extraction of the rhodium complex catalyst, the organic product is separated from the aqueous solution and withdrawn from zone 9 through line 11 and passed to distillation zone 12. In distillation zone 12 the organic product is subjected to distillation whereby the desired alcohol product is separated and passed to storage through line 14 while any unwanted by-products or unconverted starting materials are withdrawn through line 15. In addition, the tertiary amine modifier is withdrawn from zone 12 through line 13 and recycled back to zone 1 through lines 4 and 13. The aqueous portion of the mixture comprising the ammonium hydroxide solution containing the rhodium complex catalyst is passed ammonia stripping or removal zone 17 through line 16. In zone 17 the aqueous ammonium hydroxide solution is stripped of any free ammonia by contact with carbon monoxide or a carbon monoxide-containing gas which is charged to zone 17 through line 18. The carbon monoxide or carbon monoxide-containing gas which is used to strip the ammonia from the aqueous ammonium hydroxide solution in zone 17 and which contains the stripped ammonia is withdrawn from zone 17 and passed to ammonia scrubbing zone 20 through line 19. In scrubbing zone 20, the gases are contacted with water which is charged to zone 20 through line 21 and the resulting aqueous ammonium hydroxide solution and make-up ammonia or ammonium hydroxide solution are charged to extraction zone 9 through lines 27 and 28. Likewise, the carbon monoxide or carbon monoxide-containing gas is withdrawn from zone 20 and recycled to removal zone 17 through lines 18 and 22.

The aqueous solution containing the rhodium complex catalyst from which the ammonia has been stripped is withdrawn from zone 17 through line 23 and passed to water removal zone 24. Herein a portion of the water is stripped therefrom by conventional means, such as distillation, and recycled to zone 20 through lines 21 and 25. The remaining rhodium complex catalyst in a minor amount of water is withdrawn from removal zone 24 and recycled to hydroformylation zone 1 through line 26 to act as a catalyst for the hydroformylation of olefinic hydrocarbons in a manner hereinbefore set forth.

The following examples are given to illustrate the process of the present invention. However, it is to be understood that these examples are given merely for purposes of illustration and that the present invention is not necessarily limited thereto.

EXAMPLE I

In this example an olefin charge comprising 660 grams of a blend of normal hendecene with smaller amounts of aromatic and paraffinic impurities was charged to a 3 liter glass lined rotating stainless steel autoclave along with 114 grams of dimethyldodecylamine and 0.64 grams of chlorodicarbonylrhodium dimer. The autoclave was sealed and 200 atmospheres of 1:1 blend of carbon monoxide and hydrogen was charged thereto at room temperature. The autoclave was then heated to a temperature ranging from 140° to 156° C. and maintained thereat for a period of 6 hours.

During this time the maximum pressure dropped from 210 atmospheres to 133 atmospheres. At the end of the six hour period heating was discontinued and after the autoclave was allowed to return to room temperature the excess pressure was discharged and the reaction mixture was recovered therefrom. The deep red hydroformylation product was analyzed by standard gas-liquid chromatographic techniques to determine that there had been a 100% conversion of the olefin with a 93 mole % selectivity to dodecanol.

EXAMPLE II

The product obtained from Example I above in an amount of 382.6 grams along with 193.7 grams of aqueous ammonium hydroxide solution containing 30% by weight of ammonia was placed in a sealed glass flask under a nitrogen atmosphere and stirred for a period of 72 hours at room temperature. At the end of this time, the aqueous and organic phases were separated by means of a separatory funnel under a nitrogen atmosphere and portions were analyzed by atomic absorption spectroscopy for rhodium. It was determined that the distribution of rhodium consisted of 3% by weight (11 ppm) in the organic phase and 97% by weight (692 ppm) in the aqueous phase.

EXAMPLE III

A portion (161.1 grams) of the aqueous ammonium hydroxide solution containing the rhodium complex catalyst which was dark green in color was placed in a Pyrex flask at a temperature of 20° C. and 1 atmosphere of carbon monoxide was charged to the flask at a rate of 350 cc/min. The flask was heated to a temperature of 71° C. while the carbon monoxide was added for a period of 50 minutes.

At the end of this time the water was distilled out at a temperature in the range of from 47° C. to 70° C. under a pressure of from 74 to 182 mm Hg for a period of 75 minutes. This product was also dark green in color and was found to contain only 0.08% by weight of ammonia with 0.0962 grams (1980 ppm) of rhodium present in the solution. In addition, the water which was distilled contained no detectable rhodium.

The product obtained from the above paragraph may then be utilized as a catalyst for the hydroformylation of a hendecene by treating olefin at a temperature of about 150° C. and a pressure of about 200 atmospheres, said pressure being afforded by a 1:1 blend gas of carbon monoxide and hydrogen, in the presence of dimethyldodecylamine modifier.

We claim as our invention:

1. A catalytic process for the synthesis of an alcohol from an olefinic hydrocarbon wherein a substantial quantity of catalyst is recovered which comprises:
   (a) treating said olefinic hydrocarbon having at least 3 carbon atoms with carbon monoxide and hydrogen in a hydroformylation reaction zone at hydroformylation reaction conditions in the presence of a rhodium complex catalyst and a tertiary amine modifier to produce said alcohol in a homogeneous admixture with unreacted carbon monoxide, hydrogen, said rhodium catalyst and said tertiary amine modifier;
   (b) separating said unreacted carbon monoxide and hydrogen in a first separation zone from said homogeneous alcohol product admixture;
   (c) recycling at least a portion of said unreacted carbon monoxide and hydrogen to said hydroformylation reaction zone;
   (d) treating said remaining homogeneous admixture comprising said alcohol, said rhodium catalyst and said tertiary amine modifier in a catalyst extraction zone with an aqueous ammonium hydroxide solution at treatment conditions to produce;
      (i) an organic phase comprising said alcohol and said tertiary amine modifier, and
      (ii) an aqueous ammonium hydroxide solution phase comprising said rhodium catalyst, water and ammonia;
   (e) separating said organic phase in a second separation zone to produce an alcohol product stream and a tertiary amine modifier stream;
   (f) recovering said alcohol product from said alcohol product stream;
   (g) recovering said modifier from said modifier stream and recycling at least a portion of said modifier to said hydroformylation reaction zone;
   (h) stripping ammonia from said aqueous ammonium hydroxide solution phase containing said rhodium complex catalyst by contact of said phase with an ammonia stripping agent consisting essentially of carbon monoxide at a temperature ranging from about ambient up to about 150° C. and a pressure ranging from about 0.1 to about 5 atmospheres to produce an aqueous stripping phase containing water, said rhodium complex catalyst and less than about 0.5 wt % ammonia;

(i) distilling off a portion of said water from said aqueous stripping phase at water distillation conditions to produce a stream consisting essentially of rhodium catalyst and water; and (j) recycling at least a portion of said stream consisting essentially of rhodium catalyst and water to said hydroformylation reaction zone.

2. The process as set forth in claim 1 in which said hydroformylation reaction conditions include a temperature in the range of from about 50° to about 250° C. and a pressure in the range of from about 50 to about 300 atmospheres.

3. The process as set forth in claim 1 in which said rhodium extraction conditions with an aqueous ammonium hydroxide solution include a temperature in the range of from about 20° to about 100° C. and a pressure in a range of from about atmospheric to about 50 atmospheres.

4. The process as set forth in claim 1 in which said water distillation conditions include a temperature in a range of from about 50° to about 150° C. and a pressure in a range of from about 0.1 to about 5 atmospheres.

5. The process as set forth in claim 1 in which said olefinic hydrocarbon contains from 3 to about 30 carbon atoms.

6. The process as set forth in claim 1 in which said rhodium complex catalyst comprises chlorodicarbonylrhodium dimer.

7. The process as set forth in claim 1 in which said rhodium complex catalyst comprises rhodium carbonyl.

8. The process as set forth in claim 1 in which said aqueous ammonium hydroxide solution contains from about 5 to about 30% by weight of ammonia.

9. The process as set forth in claim 1 in which said olefinic hydrocarbon comprises hendecene and said alcohol comprises dodecanol.

10. The process as set forth in claim 1 in which said olefinic hydrocarbon comprises isobutylene and said alcohol comprises isopentanol.

11. The process as set forth in claim 1 in which said olefinic hydrocarbon comprises octene and said alcohol comprises nonanol.

12. The process as set forth in claim 1 in which said olefinic hydrocarbon comprises propene and said alcohol comprises butanol.

13. The process as set forth in claim 1 in which said olefinic hydrocarbon comprises nonadecene and said alcohol comprises eicosanol.

* * * * *